US008633162B2

(12) United States Patent
Acheampong et al.

(10) Patent No.: US 8,633,162 B2
(45) Date of Patent: *Jan. 21, 2014

(54) METHODS OF PROVIDING THERAPEUTIC EFFECTS USING CYCLOSPORIN COMPONENTS

(71) Applicant: Allergan, Inc., Irvine, CA (US)

(72) Inventors: Andrew Acheampong, Irvine, CA (US); Diane D. Tang-Liu, Las Vegas, NV (US); James N. Chang, Newport Beach, CA (US); David F. Power, Hubert, NC (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/967,179

(22) Filed: Aug. 14, 2013

(65) Prior Publication Data

US 2013/0338083 A1    Dec. 19, 2013

Related U.S. Application Data

(63) Continuation of application No. 13/961,818, filed on Aug. 7, 2013, which is a continuation of application No. 11/897,177, filed on Aug. 28, 2007, which is a continuation of application No. 10/927,857, filed on Aug. 27, 2004, now abandoned.

(60) Provisional application No. 60/503,137, filed on Sep. 15, 2003.

(51) Int. Cl.
*A61K 38/13*    (2006.01)

(52) U.S. Cl.
USPC ...................................... 514/20.5

(58) Field of Classification Search
None
See application file for complete search history.

(56) References Cited

U.S. PATENT DOCUMENTS

| | | | |
|---|---|---|---|
| 3,278,447 A | 10/1966 | McNicholas | |
| 4,388,229 A | 6/1983 | Fu | |
| 4,388,307 A | 6/1983 | Cavanak | |
| 4,614,736 A | 9/1986 | Delevallee et al. | |
| 4,649,047 A | 3/1987 | Kaswan | |
| 4,764,503 A | 8/1988 | Wenger | |
| 4,814,323 A | 3/1989 | Andrieu et al. | |
| 4,839,342 A | 6/1989 | Kaswan | |
| 4,970,076 A | 11/1990 | Horrobin | |
| 4,990,337 A | 2/1991 | Kurihara et al. | |
| 4,996,193 A | 2/1991 | Hewitt et al. | |
| 5,047,396 A | 9/1991 | Orban et al. | |
| 5,051,402 A | 9/1991 | Kurihara et al. | |
| 5,053,000 A | 10/1991 | Booth et al. | |
| 5,286,730 A | 2/1994 | Caufield et al. | |
| 5,286,731 A | 2/1994 | Caufield et al. | |
| 5,294,604 A | 3/1994 | Nussenblatt et al. | |
| 5,296,158 A | 3/1994 | MacGilp et al. | |
| 5,342,625 A | 8/1994 | Hauer et al. | |
| 5,368,854 A | 11/1994 | Rennick | |
| 5,411,952 A | 5/1995 | Kaswan | |
| 5,424,078 A | 6/1995 | Dziabo | |
| 5,474,919 A | 12/1995 | Chartrain et al. | |
| 5,474,979 A | 12/1995 | Ding et al. | |
| 5,504,068 A | 4/1996 | Komiya et al. | |
| 5,540,931 A | 7/1996 | Hewitt et al. | |
| 5,543,393 A | 8/1996 | Kim et al. | |
| 5,589,455 A | 12/1996 | Woo | |
| 5,591,971 A | 1/1997 | Shahar et al. | |
| 5,614,491 A | 3/1997 | Walch et al. | |
| 5,639,724 A | 6/1997 | Cavanak | |
| 5,652,212 A | 7/1997 | Cavanak et al. | |
| 5,719,123 A | 2/1998 | Morley et al. | |
| 5,739,105 A | 4/1998 | Kim et al. | |
| 5,753,166 A | 5/1998 | Dalton et al. | |
| 5,766,629 A | 6/1998 | Cho et al. | |
| 5,798,333 A | 8/1998 | Sherman | |
| 5,807,820 A | 9/1998 | Elias et al. | |
| 5,827,822 A | 10/1998 | Floch'h et al. | |
| 5,827,862 A | 10/1998 | Yamamura | |
| 5,834,017 A | 11/1998 | Cho et al. | |
| 5,843,452 A | 12/1998 | Wiedmann et al. | |
| 5,843,891 A | 12/1998 | Sherman | |
| 5,858,401 A | 1/1999 | Bhalani et al. | |
| 5,866,159 A | 2/1999 | Hauer et al. | |
| 5,891,846 A | 4/1999 | Ishida et al. | |

(Continued)

FOREIGN PATENT DOCUMENTS

DE    19810655    9/1999
EP    0471293     2/1992

(Continued)

OTHER PUBLICATIONS

Abdulrazik, M. et al, Ocular Delivery of Cyclosporin A II. Effect of Submicron Emulsion's Surface Charge on Ocular Distribution of Topical Cyclosporin A, S.T.P. Pharma Sciences, Dec. 2001, 427-432, 11(6).

Acheampong, Andrew et al, Cyclosporine Distribution into the Conjunctiva, Cornea, Lacrimal Gland and Systemic Blood Following Topical Dosing of Cyclosporine to Rabbit, Dog and Human eyes, 1996, 179.

Acheampong, Andrew et al, Cyclosporine Distribution Into the Conjunctiva, Cornea, Lacrimal Gland, and Systemic Blood Following Topical Dosing of Cyclosporine to Rabbit, Dog, and Human Eyes, Adv. Exp. Med. Biol., 1998, 1001-1004, 438.

Acheampong, Andrew et al, Distribution of Cyclosporin A in Ocular Tissues After Topical Administration to Albino Rabbits and Beagle Dogs, Current Eye Research, 1999, 91-103, 18(2).

(Continued)

*Primary Examiner* — Marcela M Cordero Garcia

(74) *Attorney, Agent, or Firm* — Laura L. Wine; Joel German

(57)    ABSTRACT

Methods of treating an eye of a human or animal include administering to an eye of a human or animal a composition in the form of an emulsion including water, a hydrophobic component and a cyclosporin component in a therapeutically effective amount of less than 0.1 % by weight of the composition. The weight ratio of the cyclosporin component to the hydrophobic component is less than 0.8.

24 Claims, No Drawings

(56) References Cited

U.S. PATENT DOCUMENTS

| | | | |
|---|---|---|---|
| 5,916,589 A | 6/1999 | Hauer et al. |
| 5,929,030 A | 7/1999 | Hamied et al. |
| 5,951,971 A | 9/1999 | Kawashima et al. |
| 5,962,014 A | 10/1999 | Hauer et al. |
| 5,962,017 A | 10/1999 | Hauer et al. |
| 5,962,019 A | 10/1999 | Cho et al. |
| 5,977,066 A | 11/1999 | Cavanak |
| 5,981,479 A | 11/1999 | Ko et al. |
| 5,981,607 A | 11/1999 | Ding et al. |
| 5,998,365 A | 12/1999 | Sherman |
| 6,004,566 A | 12/1999 | Friedman et al. |
| 6,007,840 A | 12/1999 | Hauer et al. |
| 6,008,191 A | 12/1999 | Singh |
| 6,008,192 A | 12/1999 | Al-Razzak et al. |
| 6,022,852 A | 2/2000 | Klokkers et al. |
| 6,024,978 A | 2/2000 | Hauer et al. |
| 6,046,163 A | 4/2000 | Stuchlik et al. |
| 6,057,289 A | 5/2000 | Mulye |
| 6,159,933 A | 12/2000 | Sherman |
| 6,197,335 B1 | 3/2001 | Sherman |
| 6,254,860 B1 | 7/2001 | Garst |
| 6,254,885 B1 | 7/2001 | Cho et al. |
| 6,267,985 B1 | 7/2001 | Chen et al. |
| 6,284,268 B1 | 9/2001 | Mishra et al. |
| 6,294,192 B1 | 9/2001 | Patel et al. |
| 6,306,825 B1 | 10/2001 | Cavanak |
| 6,323,204 B1 | 11/2001 | Burke |
| 6,346,511 B1 | 2/2002 | Singh et al. |
| 6,350,442 B2 | 2/2002 | Garst |
| 6,413,547 B1 | 7/2002 | Bennett et al. |
| 6,420,355 B2 | 7/2002 | Richter et al. |
| 6,468,968 B2 | 10/2002 | Cavanak et al. |
| 6,475,519 B1 | 11/2002 | Meinzer et al. |
| 6,486,124 B2 | 11/2002 | Olbrich et al. |
| 6,544,953 B2 | 4/2003 | Tsuzuki et al. |
| 6,555,526 B2 | 4/2003 | Matsuo |
| 6,562,873 B2 | 5/2003 | Olejnik et al. |
| 6,569,463 B2 | 5/2003 | Patel et al. |
| 6,582,718 B2 | 6/2003 | Kawashima |
| 6,656,460 B2 | 12/2003 | Benita et al. |
| 6,872,705 B2 | 3/2005 | Lyons |
| 6,984,628 B2 * | 1/2006 | Bakhit et al. .......... 514/20.8 |
| 7,202,209 B2 | 4/2007 | Chang |
| 7,276,476 B2 | 10/2007 | Chang et al. |
| 7,288,520 B2 | 10/2007 | Chang et al. |
| 7,297,679 B2 | 11/2007 | Chang |
| 7,501,393 B2 | 3/2009 | Tien et al. |
| 8,211,855 B2 | 7/2012 | Chang et al. |
| 8,288,348 B2 | 10/2012 | Chang et al. |
| 2001/0003589 A1 | 6/2001 | Neuer et al. |
| 2001/0014665 A1 | 8/2001 | Fischer et al. |
| 2001/0036449 A1 | 11/2001 | Garst |
| 2002/0012680 A1 | 1/2002 | Patel et al. |
| 2002/0013272 A1 | 1/2002 | Cavanak et al. |
| 2002/0016290 A1 | 2/2002 | Floc'h et al. |
| 2002/0016292 A1 | 2/2002 | Richter et al. |
| 2002/0025927 A1 | 2/2002 | Olbrich et al. |
| 2002/0045601 A1 | 4/2002 | Kawashima |
| 2002/0107183 A1 | 8/2002 | Petszulat et al. |
| 2002/0119190 A1 | 8/2002 | Meinzer et al. |
| 2002/0165134 A1 | 11/2002 | Richter et al. |
| 2003/0021816 A1 | 1/2003 | Kang et al. |
| 2003/0044452 A1 | 3/2003 | Ueno |
| 2003/0055028 A1 | 3/2003 | Stergiopoulos et al. |
| 2003/0059470 A1 | 3/2003 | Muller |
| 2003/0060402 A1 | 3/2003 | Cavanak et al. |
| 2003/0087813 A1 | 5/2003 | Or et al. |
| 2003/0104992 A1 | 6/2003 | Or et al. |
| 2003/0108626 A1 | 6/2003 | Benita et al. |
| 2003/0109425 A1 | 6/2003 | Or et al. |
| 2003/0109426 A1 | 6/2003 | Or et al. |
| 2003/0133984 A1 | 7/2003 | Ambuhl et al. |
| 2003/0143250 A1 | 7/2003 | Hauer et al. |
| 2003/0147954 A1 | 8/2003 | Yang et al. |
| 2003/0166517 A1 | 9/2003 | Fricker et al. |
| 2005/0014691 A1 | 1/2005 | Bakhit et al. |
| 2005/0059583 A1 | 3/2005 | Acheampong |
| 2007/0015691 A1 | 1/2007 | Chang |
| 2007/0027072 A1 | 2/2007 | Tien et al. |
| 2007/0087962 A1 | 4/2007 | Tien et al. |
| 2007/0149447 A1 | 6/2007 | Chang et al. |
| 2007/0299004 A1 | 12/2007 | Acheampong et al. |
| 2008/0039378 A1 | 2/2008 | Graham et al. |
| 2008/0070834 A1 | 3/2008 | Chang et al. |
| 2008/0146497 A1 | 6/2008 | Graham et al. |
| 2008/0207495 A1 | 8/2008 | Graham et al. |
| 2009/0131307 A1 | 5/2009 | Tien et al. |
| 2010/0279951 A1 | 11/2010 | Morgan et al. |
| 2011/0009339 A1 | 1/2011 | Schiffman |
| 2011/0294744 A1 | 12/2011 | Morgan et al. |
| 2012/0270805 A1 | 10/2012 | Chang et al. |
| 2013/0059796 A1 | 3/2013 | Chang et al. |

FOREIGN PATENT DOCUMENTS

| | | |
|---|---|---|
| EP | 0547229 | 1/1993 |
| EP | 0760237 | 3/1997 |
| WO | 95-31211 | 11/1995 |
| WO | 00-00179 | 1/2000 |
| WO | 01-32142 | 5/2001 |
| WO | 01-41671 | 6/2001 |
| WO | 02-09667 | 2/2002 |
| WO | 02-49603 | 6/2002 |
| WO | 03-030834 | 4/2003 |
| WO | 03-053405 | 7/2003 |

OTHER PUBLICATIONS

Akpek, Esen Karamursel et al, A Randomized Trial of Topical Cyclosporin 0.05% in Topical Steroid-Resistant Atopic Keratoconjunctivitis, Ophthalmology, 2004, 476-482, 111.

Angelov, O. et al, Preclinical Safety Studies of Cyclosporine Ophthalmic Emulsion, Adv Exp Med Biol, 1998, 991-995, 438.

Angelov, O. et al, Safety Assessment of Cyclosporine Ophthalmic Emulsion in Rabbits and Dogs, XIth Congress of the European Society of Ophthalmology, 1997, 25-28, 1-5, Soc. Ophthalmol Eur., Hu.

Ardizzone Sandro et al, A Practical Guide to the Management of Distal Ulceratve Colitis, Drugs, 1998, 519-542, 55(4).

Banic, Marko et al, Effect of Cyclosporine in a Murine Model of Experimental Colitis, Digestve Diseases and Sciences, Jun. 2002, 1362-1368, 47(6).

Bonini, S. et al, Vernal Keratoconjunctivitis, Eye, 2004, 345-351, 18.

Brewster, Marcus et al, Enhanced Delivery of Ganciclovir to the Brain Though the Use of Redox Targeting, Antimicrobial Agents and Chemotherapy, Apr. 1994, 817-823, 38(4).

Brewster, Marcus et al, Intravenous and Oral Pharmacokinetic Evaluation of a 2-Hydroxypropyl-β-cyclodextrin-Based Formulation of Carbamazepine in the Dog: Comparison with Commercially Available Tablets and Suspensions, Journal of Pharmaceutical Sciences, Mar. 1997, 335-339, 86(3).

Brewster, Marcus et al, Preparation, Characterization, and Anesthetic Properties of 2-Hydroxypropyl-β-cyclodextrin Complexes of Pregnanolone and Pregnenolone in Rat and Mouse, Journal of Pharmaceutical Sciences, Oct. 1995, 1154-1159, 84(10).

Brinkmeier, Thomas et al, Pyodermatitis-Pyostomatitis Vegetans: A Clinical Course of Two Decades with Response to Cyclosporine and Low-Dose Prednisolone, Acta Derm Venereol, 2001, 134-136, 81.

Castillo, Jose M. Benitez Del et al, Influence of Topical Cyclosporine A and Dissolvent on Corneal Epithelium Permeability of Fluorescein, Documenta Ophthalmologica, 1995, 49-55, 91.

Cheeks, Lisa et al, Influence of Vehicle and Anterior Chamber Protein Concentration on Cyclosporine Penetration Through the Isolated Rabbit Cornea, Current Eye Research, 1992, 641-649, 11(7).

Database WPI Week 200044, Derwent Pub. Ltd., London, GB; An 2000-492678 & JP2000/143542, 2000, 2 Pages.

Ding, Shulin et al, Cyclosporine Ophthalmic O/W emulsion: Formulation and Emulsion Characterization, Pharm Res, 1997, 1 page, 14 (11).

Donnenfeld, Eric D., The Economics of Using Restasis, Ophthalmology Management, Oct. 2003, 3 pages, US.

Drosos, A. A. et al, Efficacy and Safety of Cyclosporine-A Therapy for Primary Sjogren's Syndrome, Ter. Arkh., 1998, 77-80, 60(4).

(56) References Cited

OTHER PUBLICATIONS

Drosos, A.A. et al, Cyclosporin A Therapy in Patients with Primary Sjogren's Syndrome: Results at One Year, Scand J Rheumatology, 1986, 246-249, 61.
Eisen, Drore et al, Topical Cyclosporine for Oral Mucosal Disorders, J Am Acad Dermatol, Dec. 1990, 1259-1264, 23.
Epstein, Joel et al, Topical Cyclosporine in a Bioadhesive for Treatment of Oral Lichenoid Muscosal Reactions, Oral Surg Oral Med Oral Pathol Oral, 1996, 532-536, 82.
Erdmann, S. et al, Pemphigus Vulgaris Der Mund- Und Kehlkopfschleimhaut Pemphigus Vulgaris of the Oral Mucosa and the Larynx, H+G Zeitschrift Fuer Hautkrankheiten, 1997, 283-286, 72(4).
FDA Concludes Restasis (Cyclosporine) Not Effective for Dry Eye (Jun. 18, 1999). Accessed online at http://www.dryeyeinfo.org/Restasis_Cyclosporine.htm on Aug. 14, 2009. 1 Page.
Gaeta, G.M. et al, Cyclosporin Bioadhesive Gel in the Topical Treatment of Erosive Oral Lichen Planus, International Journal of Immunopathology and Pharmacology, 1994, 125-132, 7(2).
Gipson, Ilene et al, Character of Ocular Surface Mucins and Their Alteration in Dry Eye Disease, The Ocular Surface, Apr. 2004, 131-148, 2(2).
Gremse, David et al, Ulcerative Colitis in Children, Pediatr Drugs, 2002, 807-815, 4(12).
Gunduz, Kaan et al, Topical Cyclosporin Treatment of Keratoconjunctivitis Sicca in Secondary Sjogren's Syndrome, Acta Ophthalmologica, 1994, 438-442, 72.
http://web.archive.org/web/2001030625323/http://www.surfactant.co.kr/surfactants/pegester.html, 2001, 6 Pages, retrieved on Jul. 5, 2008.
Hunter, P.A. et al, Cyclosporin A Applied Topically to the Recipient Eye Inhibits Corneal Graft Rejection, Clin Exp Immunol, 1981, 173-177, 45.
Jumaa, Muhannad et al, Physicochemical Properties and Hemolytic Effect of Different Lipid Emulsion Formulations Using a Mixture of Emulsifiers, Pharmaceutica Acta Helvetiae, 1999, 293-301, 73.
Kanai, A. et al, The Effect on the Cornea of Alpha Cyclodextrin Vehicle for Eye Drops, Transplantation Proceedings, Feb. 1989, 3150-3152, vol. 21.
Kanpolat, Ayfer et al, Penetration of Cyclosporin A into the Rabbit Cornea and Aqueous Humor after Topical Drop and Collagen Shield Administration, Cornea/External Disease, Apr. 1994, 119-122, 20(2).
Kaur, Rabinder et al, Solid Dispersions of Drugs in Polyocyethylene 40 Stearate: Dissolution Rates and Physico-Chemical Interactions, Journal of Pharmacy and Pharmacology, Dec. 1979, 48P.
Kuwano, Mitsuaki et al, Cyclosporine A Formulation Affects Its Ocular Distribution in Rabbits, Pharmaceutical Research, Jan. 2002, 108-111, 19(1).
Lambert Technologies Corp. Material Safety Data Sheet for LUMULSE™ POE-40 MS KP, last revision Aug. 22, 2003. 3 pages.
Leibovitz, Z. et al., Our Experience In Processing Maize (Corn) Germ Oil, Journal of the American Oil Chemists Society, Feb. 1983, 395-399, 80 (2), US.
Lixin, Xie et al, Effect of Cyclosporine A Delivery System in Corneal Transplantation, Chinese Medical Journal, 2002, 110-113, 115 (1), US.
Lopatin, D.E., Chemical Compositions and Functions of Saliva, Aug. 24, 2001, 31 Pages.
Lyons, R.T. et al, Influence of Three Emulsion Formulation Parameters on the Ocular Bioavailability of Cyclosporine A in Albino Rabbits, Am Assoc Pharm Sci, 2000, 1 Page, 2(4).
Pedersen, Anne Marie et al, Primary Sjogren's Syndrome: Oral Aspects on Pathogenesis, Diagnostic Criteria, Clinical Features and Approaches for Therapy, Expert Opin Pharma, 2001, 1415-1436, 2(9).
Phillips, Thomas et al, Cyclosporine Has a Direct Effect on the Differentiation of a Mucin-Secreting Cell Line, Journal of Cellular Physiology, 2000, 400-408, 184.
Present, D.H. et al, Cyclosporine and Other Immunosuppressive Agents: Current and Future Role in the Treatment of Inflammatory Bowel Disease, American Journal of Gastroenterology, 1993, 627-630, 88(5).
Restasis® Product Information Sheet, Allergan, Inc., 2009, 5 Pages.
Restasis® Increasing Tear Production, Retrieved on Aug. 14, 2009, http://www.restasisprofessional.com/_clinical/clinical_increasing.htm 3 pages.
Robinson, N.A. et al, Desquamative Gingivitis: A Sign of Mucocutaneous Disorders—a Review, Australian Dental Journal, 2003, 205-211, 48(4).
Rudinger, J., Characteristics of the Amino Acids as Components of a Peptide Hormone Sequence, Peptide Hormones, 1976, 1-7.
Sall, Kenneth et al, Two Multicenter, Randomized Studies of the Efficacy and Safety of Cyclosporine Ophthalmic Emulsion in Moderate to Severe Dry Eye Disease, Ophthalmology, 2000, 631-639, 107.
Sandborn, William et al, A Placebo-Controlled Trial of Cyclosporine Enemas for Mildly to Moderately Active Left-Sided Ulcerative Colitis, Gastroenterology, 1994, 1429-1435, 106.
Sandborn, William et al, Cyclosporine Enemas for Treatment-Resistant, Mildly to Moderately Active, Left-Sided Ulcerative Colitis, American Journal of Gastroenterology, 1993, 640-645, 88(5).
Schwab, Matthias et al, Pharmacokinetic Considerations in the Treatment of Inflammatory Bowel Disease, Clin Pharm, 2001, 723-751, 60(10).
Secchi, Antonio et al, Topical Use of Cyclosporine in the Treatment of Vernal Keratoconjunctivitis, American Journal of Ophthalmology, Dec. 1990, 641-645, 110.
Small, Dave et al, The Ocular Pharmacokinetics of Cyclosporine in Albino Rabbits and Beagle Dogs, Ocular Drug Delivery and Metabolism, 1999, 54.
Small, David et al, Blood Concentrations of Cyclosporin A During Long-Term Treatment With Cyclosporin A ophthalmic Emulsions in Patients with Moderate to Severe Dry Eye Disease, Journal of Ocular Pharmacology and Therapeutics, 2002, 411-418, 18(5).
Smilek, Dawn et al, A Single Amino Acid Change in a Myelin Basic Protein Peptide Confers the Capacity to Prevent Rather Than Induce Experimental Autoimmune Encephalomyelitis, Proc. Natl. Acad. Sci., Nov. 1991, 9633-9637, 88.
Stephenson, Michelle, The Latest Uses of Restasis, Review of Ophthalmology, Dec. 30, 2005, 7 Pages, US.
Stevenson, Dara et al, Efficacy and Safety of Cyclosporin A ophthalmic Emulsion in the Treatment of Moderate-to-Severe Dry Eye Disease, Ophthalmology, 2000, 967-974, 107.
Tesavibul, N. et al, Topical Cyclosporine A (CsA) for Ocular Surface Abnormalities in Graft Versus Host Disease Patients, Invest Ophthalmol Vis Sci, Feb. 1996, S1026, 37(3).
The Online Medical Dictionary, Derivative, Analog, Analogue, Xerostomia, accessed Jul. 7, 2005 and Jul. 13, 2005, 6 Pages.
Tibell, A. et al., Cyclosporin A In Fat Emulsion Carriers: Experimental Studies on Pharmacokinetics and Tissue Distribution, Pharmacology & Toxicology, 1995, 115-121, 76, US.
Tsubota, Kazuo et al, Use of Topical Cyclosporin A in a Primary Sjogren's Syndrome Mouse Model, Invest Ophthalmol Vis Sci, Aug. 1998, 1551-1559, 39(9).
Van Der Reijden, Willy et al, Treatment of Oral Dryness Related Complaints (Xerostomia) in Sjogren's Syndrome, Ann Rheum Dis, 1999, 465-473, 58.
Winter, T.A. et al, Cyclosporin A Retention Enemas in Refractory Distal Ulcerative Colitis and 'Pouchitis', Scand J Gastroenterol, 1993, 701-704, 28.
Pending U.S. Appl. No. 13/967,189, filed Aug. 14, 2013.
Pending U.S. Appl. No. 13/961,818, filed Aug. 7, 2013.
Pending U.S. Appl. No. 13/961,828, filed Aug. 7, 2013.
Pending U.S. Appl. No. 13/961,835, filed Aug. 7, 2013.
Pending U.S. Appl. No. 13/961,808, filed Aug. 7, 2013.
Pending U.S. Appl. No. 13/967,163, filed Aug. 14, 2013.
Pending U.S. Appl. No. 13/967,168, filed Aug. 14, 2013.
U.S. Re-Examination Application: 90/009,944 Filed on Aug. 27, 2011.

* cited by examiner

METHODS OF PROVIDING THERAPEUTIC EFFECTS USING CYCLOSPORIN COMPONENTS

RELATED APPLICATION

This application is a continuation of copending U.S. application Ser. No. 13/961,818 filed Aug. 7, 2013, which is a continuation of copending U.S. application Ser. No. 11/897,177, filed Aug. 28, 2007, which is a continuation of U.S. application Ser. No. 10/927,857, filed Aug. 27, 2004, now abandoned, which claimed the benefit of U.S. Provisional Application No. 60/503,137 filed Sep. 15, 2003, which are incorporated in their entirety herein by reference.

BACKGROUND OF THE INVENTION

The present invention relates to methods of providing desired therapeutic effects to humans or animals using compositions including cyclosporin components. More particularly, the invention relates to methods including administering to an eye of a human or animal a therapeutically effective amount of a cyclosporin component to provide a desired therapeutic effect, preferably a desired ophthalmic or ocular therapeutic effect.

The use of cyclosporin-A and cyclosporin A derivatives to treat ophthalmic conditions has been the subject of various patents, for example Ding et al U.S. Pat. No. 5,474,979; Garst U.S. Pat. No. 6,254,860; and Garst U.S. Pat. No. 6,350,442, this disclosure of each of which is incorporated in its entirely herein by reference. In addition, cyclosporin A compositions used in treating ophthalmic conditions is the subject of a number of publications. Such publications include, for example, "*Blood concentrations of cyclosporin a during long-term treatment with cyclosporin a ophthalmic emulsions in patients with moderate to severe dry eye disease,*" Small et al, *J Ocul Pharmacol Ther,* 2002 October, 18(5):411-8; "*Distribution of cyclosporin A in ocular tissues after topical administration to albino rabbits and beagle dogs,*" Acheampong et al, *Curr Eye Res,* 1999 February, 18(2):91-103b; "*Cyclosporine distribution into the conjunctiva, cornea, lacrimal gland, and systemic blood following topical dosing of cyclosporine to rabbit, dog, and human eyes,*" Acheampong et al, *Adv Exp Med Biol,* 1998, 438:1001-4; "*Preclinical safety studies of cyclosporine ophthalmic emulsion,*" Angelov et al, *Adv Exp Med Biol,* 1998, 438:991-5; "*Cyclosporin & Emulsion & Eye,*" Stevenson et al, Ophthalmology, 2000 May, 107(5):967-74; and "*Two multicenter, randomized studies of the efficacy and safety of cyclosporine ophthalmic emulsion in moderate to severe dry eye disease. CsA Phase 3 Study Group,*" Sall et al, *Ophthalmology,* 2000 April, 107(4):631-9. Each of these publications is incorporated in its entirety herein by reference. In addition, cyclosporin A-containing oil-in-water emulsions have been clinically tested, under conditions of confidentiality, since the mid 1990's in order to obtain U.S. Food and Drug Administration (FDA) regulatory approval.

Examples of useful cyclosporin A-containing emulsions are set out in Ding et al U.S. Pat. No. 5,474,979. Example 1 of this patent shows a series of emulsions in which the ratio of cyclosporin A to castor oil in each of these compositions was 0.08 or greater, except for Composition B, which included 0.2% by weight cyclosporin A and 5% by weight castor oil. The Ding et al patent placed no significance in Composition B relative to Compositions A, C and D of Example 1.

Over time, it has become apparent that cyclosporin A emulsions for ophthalmic use preferably have less than 0.2% by weight of cyclosporin A. With cyclosporin A concentrations less than 0.2%, the amount of castor oil employed has been reduced since one of the functions of the castor oil is to solubilize the cyclosporin A. Thus, if reduced amounts of cyclosporin are employed, reduced amounts of castor oil are needed to provide effective solubilization of cyclosporin A.

There continues to be a need for providing enhanced methods of treating ophthalmic or ocular conditions with cyclosporin-containing emulsions.

SUMMARY OF THE INVENTION

New methods of treating a human or animal using cyclosporin component-containing emulsions have been discovered. Such methods provide substantial overall efficacy in providing desired therapeutic effects. In addition, other important benefits are obtained employing the present methods. For example, patient safety is enhanced. In particular, the present methods provide for reduced risks of side effects and/or drug interactions. Prescribing physicians advantageously have increased flexibility in prescribing such methods and the compositions useful in such methods, for example, because of the reduced risks of harmful side effects and/or drug interactions. The present methods can be easily practiced.

In short, the present methods provide substantial and acceptable overall efficacy, together with other advantages, such as increased safety and/or flexibility.

In one aspect of the present invention, the present methods comprise administering to an eye of a human or animal a composition in the form of an emulsion comprising water, a hydrophobic component and a cyclosporin component in a therapeutically effective amount of less than 0.1% by weight of the composition. The weight ratio of the cyclosporin component to the hydrophobic component is less than 0.08.

It has been found that the relatively increased amounts of hydrophobic component together with relatively reduced, yet therapeutically effective, amounts of cyclosporin component provide substantial and advantageous benefits. For example, the overall efficacy of the present compositions, for example in treating dry eye disease, is substantially equal to an identical composition in which the cyclosporin component is present in an amount of 0.1% by weight. Further, a relatively high concentration of hydrophobic component is believed to provide for a more quick or rapid breaking down or resolving of the emulsion in the eye, which reduces vision distortion which may be caused by the presence of the emulsion in the eye and/or facilitates the therapeutic effectiveness of the composition. Additionally, and importantly, using reduced amounts of the active cyclosporin component mitigates against undesirable side effects and/or potential drug interactions.

In short, the present invention provides at least one advantageous benefit, and preferably a plurality of advantageous benefits.

The present methods are useful in treating any suitable condition which is therapeutically sensitive to or treatable with cyclosporin components. Such conditions preferably are ophthalmic or ocular conditions, that is relating to or having to do with one or more parts of an eye of a human or animal. Included among such conditions are, without limitation, dry eye syndrome, phacoanaphylactic endophthalmitis, uveitis, vernal conjunctivitis, atopic kerapoconjunctivitis, corneal graft rejection and the like conditions. The present invention is particularly effective in treating dry eye syndrome.

Employing reduced concentrations of cyclosporin component, as in the present invention, is advantageously effective to provide the blood of the human or animal under treatment with reduced concentrations of cyclosporin component, preferably with substantially no detectable concentration of the cyclosporin component. The cyclosporin component concentration of blood can be advantageously measured using a validated liquid chromatography/mass spectrometry-mass spectrometry (VLC/MS-MS) analytical method, such as described elsewhere herein.

In one embodiment, in the present methods the blood of the human or animal has concentrations of clyclosporin component of 0.1 ng/ml or less.

Any suitable cyclosporin component effective in the present methods may be used.

Cyclosporins are a group of nonpolar cyclic oligopeptides with known immunosuppressant activity. Cyclosporin A, along with several other minor metabolites, cyclosporin B through I, have been identified. In addition, a number of synthetic analogs have been prepared.

In general, commercially available cyclosporins may contain a mixture of several individual cyclosporins which all share a cyclic peptide structure consisting of eleven amino acid residues with a total molecular weight of about 1,200, but with different substituents or configurations of some of the amino acids.

The term "cyclosporin component" as used herein is intended to include any individual member of the cyclosporin group and derivatives thereof, as well as mixtures of two or more individual cyclosporins and derivatives thereof.

Particularly preferred cyclosporin components include, without limitation, cyclosporin A, derivatives of cyclosporin A and the like and mixtures thereof. Cyclosporin A is an especially useful cyclosporin component.

Any suitable hydrophobic component may be employed in the present invention. Advantageously, the cyclosporin component is solubilized in the hydrophobic component. The hydrophobic component may be considered as comprising a discontinuous phase in the presently useful cyclosporin component-containing emulsions.

The hydrophobic component preferably is present in the emulsion compositions in an amount greater than about 0.625% by weight. For example, the hydrophobic component may be present in an amount of up to about 1.0% by weight or about 1.5% by weight or more of the composition.

Preferably, the hydrophobic component comprises one or more oily materials. Examples of useful oil materials include, without limitation, vegetable oils, animal oils, mineral oils, synthetic oils and the like and mixtures thereof. In a very useful embodiment, the hydrophobic component comprises one or more higher fatty acid glycerides. Excellent results are obtained when the hydrophobic component comprises castor oil.

The presently useful compositions may include one or more other components in amounts effective to facilitate the usefulness and effectiveness of the compositions. Examples of such other components include, without limitation, emulsifier components, tonicity components, polyelectrolyte components, surfactant components, viscosity inducing components, acids and/or bases to adjust the pH of the composition, buffer components, preservative components and the like. Components may be employed which are effective to perform two or more functions in the presently useful compositions. For example, components which are effective as both emulsifiers and surfactants may be employed, and/or components which are effective as both polyelectrolyte components and viscosity inducing components may be employed. The specific composition chosen for use in the present invention advantageously is selected taking into account various factors present in the specific application at hand, for example, the desired therapeutic effect to be achieved, the desired properties of the compositions to be employed, the sensitivities of the human or animal to whom the composition is to be administered, and the like factors.

The presently useful compositions advantageously are ophthalmically acceptable. A composition, component or material is ophthalmically acceptable when it is compatible with ocular tissue, that is, it does not cause significant or undue detrimental effects when brought into contact with ocular tissues.

Such compositions have pH's within the physiological range of about 6 to about 10, preferably in a range of about 7.0 to about 8.0 and more preferably in a range of about 7.2 to about 7.6.

The present methods preferably provide for an administering step comprising topically administering the presently useful compositions to the eye or eyes of a human or animal.

Each and every feature described herein, and each and every combination of two or more of such features, is included within the scope of the present invention provided that the features included in such a combination are not mutually inconsistent.

These and other aspects and advantages of the present invention are apparent in the following detailed description, example and claims.

DETAILED DESCRIPTION

The present methods are effective for treating an eye of a human or animal. Such methods, in general, comprise administering, preferably topically administering, to an eye of a human or animal a cyclosporin component-containing emulsion. The emulsion contains water, for example U.S. pure water, a hydrophobic component and a cyclosporin component in a therapeutically effective amount of less than 0.1% by weight of the emulsion. In addition, beneficial results have been found when the weight ratio of the cyclosporin component to the hydrophobic component is less than 0.08.

As noted above, the present administering step preferably includes topically administering the emulsion to the eye of a patient of a human or animal. Such administering may involve a single use of the presently useful compositions, or repeated or periodic use of such compositions, for example, as required or desired to achieve the therapeutic effect to be obtained. The topical administration of the presently useful composition may involve providing the composition in the form of eye drops or similar form or other form so as to facilitate such topical administration.

The present methods have been found to be very effective in providing the desired therapeutic effect or effects while, at the same time, substantially reducing, or even substantially eliminating, side effects which may result from the presence of the cyclosporin component in the blood of the human or animal being treated, and eye irritation which, in the past, has been caused by the presence of certain components in prior art cyclosporin-containing emulsions. Also, the use of the present compositions which include reduced amounts of the cyclosporin components allow for more frequent administration of the present compositions to achieve the desired therapeutic effect or effects without substantially increasing the risk of side effects and/or eye irritation.

The present methods are useful in treating any condition which is therapeutically sensitive to or treatable with cyclosporin components. Such conditions preferably are ophthalmic or ocular conditions, that is relating to or having to do with one or more parts of an eye of a human or animal. Included among such conditions are, without limitation, dry eye syndrome, phacoanaphylactic endophthalmitis, uveitis, vernal conjunctivitis, atopic kerapoconjunctivitis, corneal graft rejection and the like conditions. The present invention is particularly effective in treating dry eye syndrome.

The frequency of administration and the amount of the presently useful composition to use during each administration varies depending upon the therapeutic effect to be obtained, the severity of the condition being treated and the like factors. The presently useful compositions are designed to allow the prescribing physician substantial flexibility in treating various ocular conditions to achieve the desired therapeutic effect or effects with reduced risk of side effects and/or eye irritation. Such administration may occur on an as needed basis, for example, in treating or managing dry eye syndrome, on a one time basis or on a repeated or periodic basis once, twice, thrice or more times daily depending on the needs of the human or animal being treated and other factors involved in the application at hand.

One of the important advantages of the present invention is the reduced concentration of the cyclosporin component in the blood of the human or animal as a result of administering the present composition as described herein. One very useful embodiment of the present administering step provides no substantial detectable concentration of cyclosporin component in the blood of the human or animal. Cyclosporin component concentration in blood preferably is determined using a liquid chromatography-mass spectroscopy-mass spectroscopy (LC-MS/MS), which test has a cyclosporin component detection limit of 0.1 ng/ml. Cyclosporin component concentrations below or less than 0.1 ng/ml are therefore considered substantially undetectable.

The LC-MS/MS test is advantageously run as follows.

One ml of blood is acidified with 0.2 ml of 0.1 N HCl solution, then extracted with 5 ml of methyl t-butyl ether. After separation from the acidified aqueous layer, the organic phase is neutralized with 2 ml of 0.1 N NaOH, evaporated, reconstituted in a water/acetonitrile-based mobil phase, and injected onto a 2.1×50 mm, 3 μm pore size C-8 reverse phase high pressure liquid chromatography (HPLC) column (Keystone Scientific, Bellefonte, Pa.). Compounds are gradient-eluted at 0.2 mL/min and detected using an API III triple quadrupole mass spectrometer with a turbo-ionspray source (PE-Sciex, Concord, Ontario, Canada). Molecular reaction monitoring enhances the sensitivity and selectivity of this assay. Protonated molecules for the analyte and an internal standard are collisionally dissociated and product ions at m/z 425 are monitored for the analyte and the internal standard. Under these conditions, cyclosporin A and the internal standard cyclosporin G elute with retention times of about 3.8 minutes. The lower limit of quantitation is 0.1 ng/mL, at which concentration the coefficient of variation and deviation from nominal concentration is <15%.

As noted previously, any suitable cyclosporin component effective in the present methods may be employed. Very useful cyclosporin components include, without limitation, cyclosporin A, derivatives of cyclosporin A and the like and mixtures thereof.

The chemical structure for cyclosporin A is represented by Formula 1

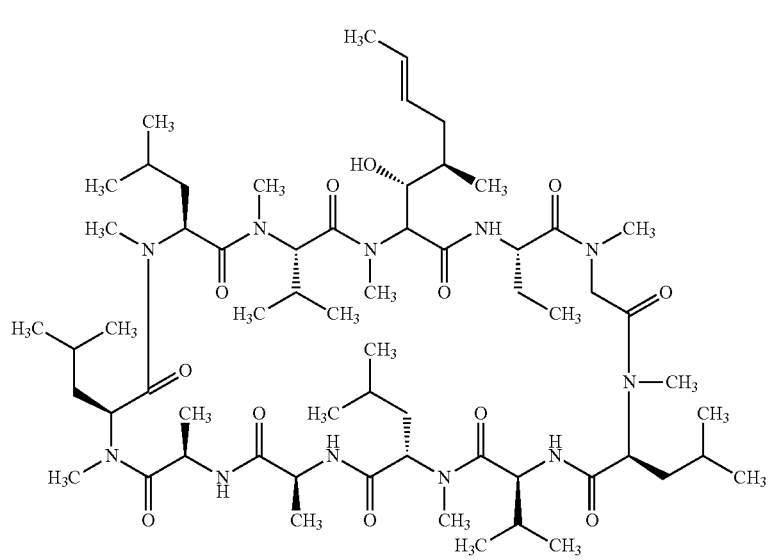

Formula I

As used herein the term "derivatives" of a cyclosporin refer to compounds having structures sufficiently similar to the cyclosporin so as to function in a manner substantially similar to or substantially identical to the cyclosporin, for example, cyclosporin A, in the present methods. Included, without limitation, within the useful cyclosporin A derivatives are those selected from ((R)-methylthio-Sar)³-(4'-hydroxy-MeLeu) cyclosporin A, ((R)-(Cyclo)alkylthio-Sar)³-(4'-hydroxy-MeLeu)⁴-cyclosporin A, and ((R)-(Cyclo)alkylthio-Sar)³-cyclosporin A derivatives described below.

These cyclosporin derivatives are represented by the following general formulas (II), (III), and (IV) respectively:
Formula II
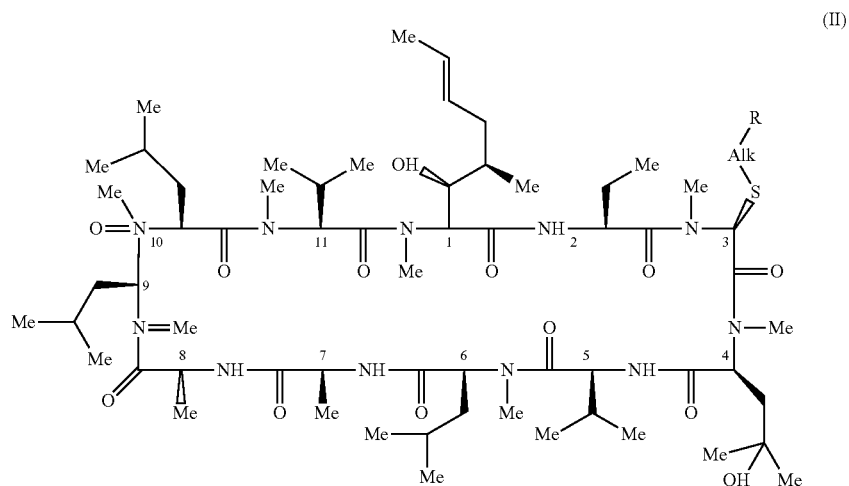
(II)
Formula III
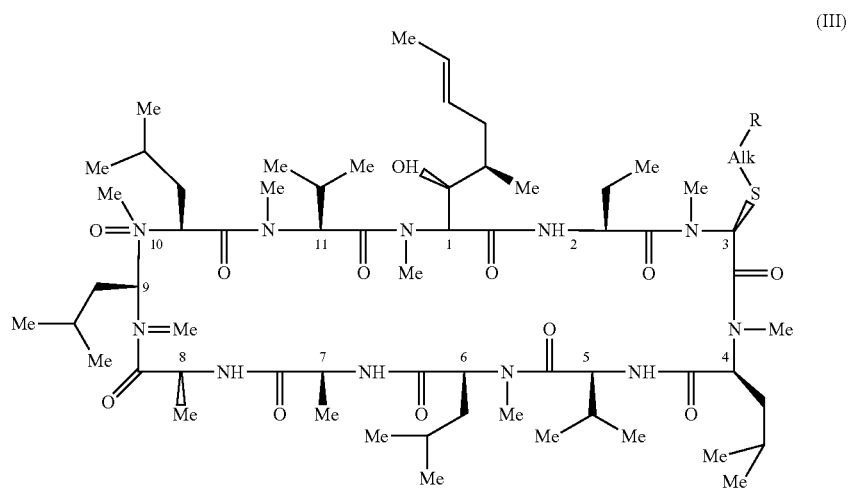
(III)
Formula IV
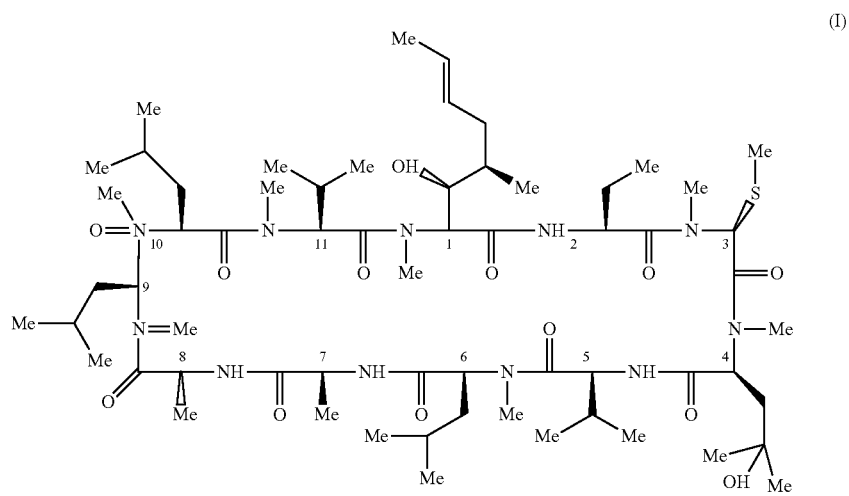
(I)

wherein Me is methyl; Alk is 2-6C alkylene or 3-6C cycloalkylene; R is OH, COOH, alkoxycarbonyl, —NR$_1$R$_2$ or N(R$_3$)—(CH$_2$)—NR$_1$R$_2$; wherein R$_1$, R$_2$ is H, alkyl, 3-6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1-3 heteroatoms; or NR$_1$R$_2$ is a 5 or 6 membered heterocycle which may contain a further N, O or S heteroatom and may be alkylated; R$_3$ is H or alkyl and n is 2-4; and the alkyl moieties contain 1-4C.

In one embodiment, the cyclosporin component is effective as an immunosuppressant. Without wishing to be limited to any particular theory of operation, it is believed that, in certain embodiments of the present invention, the cyclosporin component acts to enhance or restore lacrimal gland tearing in providing the desired therapeutic effect.

One important feature of the present invention is that the presently useful compositions contain less than 0.1% by weight of the cyclosporin component. The advantages of such low-concentrations of cyclosporin components have been discussed in some detail elsewhere herein. Low concentrations of cyclosporin component, together with concentrations of the hydrophobic component such that the weight ratio of cyclosporin component to hydrophobic component is greater than 0.08, provides one or more substantial advantages in the present methods.

Any suitable hydrophobic component may be employed in the present invention. Such hydrophobic component may be considered as comprising a discontinuous phase in the presently useful cyclosporin component-containing emulsions, with the water or aqueous phase being considered the continuous phase in such emulsion. The hydrophobic component is preferably selected so as to solubilize the cyclosporin component, which is often substantially insoluble in the aqueous phase. Thus, with a suitable hydrophobic component included in the presently useful emulsions, the cyclosporin component is preferably solubilized in the emulsions.

In one very useful embodiment, the hydrophobic component comprises an oily material, in particular, a material which is substantially not miscible in water. Examples of useful oily materials include, without limitation, vegetable oils, animal oils, mineral oils, synthetic oils, and the like and mixtures thereof. Thus, the present hydrophilic components may comprise naturally occurring oils, including, without limitation refined naturally occurring oils, or naturally occurring oils which have been processed to alter their chemical structures to some extent or oils which are substantially entirely synthetic. One very useful hydrophobic component includes higher fatty acid glycerides.

Examples of useful hydrophobic components include, without limitation, olive oil, arachis oil, castor oil, mineral oil, silicone fluid and the like and mixtures thereof. Higher fatty acid glycerides such as olive oil, peanut oil, castor oil and the like and mixtures thereof are particularly useful in the present invention. Excellent results are obtained using a hydrophobic component comprising castor oil. Without wishing to limit the invention to any particular theory of operation, it is believed that castor oil includes a relatively high concentration of ricinoleic acid which itself may be useful in benefitting ocular tissue and/or in providing one or more therapeutic effects when administered to an eye.

The hydrophobic component is preferably present in the presently useful cyclosporin component-containing emulsion compositions in an amount greater than about 0.625% by weight. For example, the hydrophobic component may be present in an amount up to about 0.75% by weight or about 1.0% by weight or about 1.5% by weight or more of the presently useful emulsion compositions.

The presently useful compositions may include one or more other components in amounts effective to facilitate the usefulness and effectiveness of the present methods and/or the presently useful compositions. Examples of such other components include, without limitation, emulsifier components, surfactant components, tonicity components, poly electrolyte components, emulsion stability components, viscosity inducing components, demulcent components, acid and/or bases to adjust the pH of the composition, buffer components, preservative components and the like.

In one very useful embodiment, the presently useful compositions are substantially free of preservatives. Thus, the presently useful compositions may be sterilized and maintained in a sterile condition prior to use, for example, provided in a sealed package or otherwise maintained in a substantially sterile condition.

Any suitable emulsifier component may be employed in the presently useful compositions, provided, that such emulsifier component is effective in forming maintaining the emulsion and/or in the hydrophobic component in emulsion, while having no significant or undue detrimental effect or effects on the compositions during storage or use.

In addition, the presently useful compositions, as well as each of the components of the present compositions in the concentration present in the composition advantageously are ophthalmically acceptable.

Useful emulsifier components may be selected from such component which are conventionally used and well known in the art. Examples of such emulsifier components include, without limitation, surface active components or surfactant components which may be anionic, cationic, nonionic or amphoteric in nature. In general, the emulsifier component includes a hydrophobic constituent and a hydrophilic constituent. Advantageously, the emulsifier component is water soluble in the presently useful compositions. Preferably, the emulsifier component is nonionic. Specific examples of suitable emulsifier components include, without limitation, polysorbate 80, polyoxyalkylene alkylene ethers, polyalkylene oxide ethers of alkyl alcohols, polyalkylene oxide ethers of alkylphenols, other emulsifiers/surfactants, preferably nonionic emulsifiers/surfactants, useful in ophthalmic compositions, and the like and mixtures thereof.

The emulsifier component is present in an amount effective in forming the present emulsion and/or in maintaining the hydrophobic component in emulsion with the water or aqueous component. In one preferred embodiment, the emulsifier component is present in an amount in a range of about 0.1% to about 5%, more preferably about 0.2% to about 2% and still more preferably about 0.5% to about 1.5% by weight of the presently useful compositions.

Polyelectrolyte or emulsion stabilizing components may be included in the presently useful compositions. Such components are believed to be effective in maintaining the electrolyte balance in the presently useful emulsions, thereby stabilizing the emulsions and preventing the emulsions from breaking down prior to use. In one embodiment, the presently useful compositions include a polyanionic component effective as an emulsion stabilizing component. Examples of suitable polyanionic components useful in the presently useful compositions include, without limitation, anionic cellulose derivatives, anionic acrylic acid-containing polymers, anionic methacrylic acid-containing polymers, anionic amino acid-containing polymers and the like and mixtures thereof.

A particularly useful class of polyanionic components include one or more polymeric materials having multiple anionic charges. Examples include, but are not limited to:

- metal carboxy methylcelluloses
- metal carboxy methylhydroxyethylcelluloses
- metal carboxy methylstarchs
- metal carboxy methylhydroxyethylstarchs
- hydrolyzed polyacrylamides and polyacrylonitriles
- heparin
- gucoaminoglycans
- hyaluronic acid
- chondroitin sulfate
- dermatan sulfate
- peptides and polypeptides
- alginic acid
- metal alginates
- homopolymers and copolymers of one or more of:
- acrylic and methacrylic acids
- metal acrylates and methacrylates
- vinylsulfonic acid
- metal vinylsulfonate
- amino acids, such as aspartic acid, glutamic acid and the like
- metal salts of amino acids
- p-styrenesulfonic acid
- metal p-styrenesulfonate
- 2-methacryloyloxyethylsulfonic acids
- metal 2-methacryloyloxethylsulfonates
- 3-methacryloyloxy-2-hydroxypropylsulonic acids
- metal 3-methacryloyloxy-2-hydroxypropylsulfonates
- 2-acrylamido-2-methylpropanesulfonic acids
- metal 2-acrylamido-2-methylpropanesulfonates
- allylsulfonic acid
- metal allylsulfonate and the like.

One particularly useful emulsion stabilizing component includes crosslinked polyacrylates, such as carbomers and Pemulen® materials. Pemulen® is a registered trademark of B.F. Goodrich for polymeric emulsifiers and are commercially available from B.F. Goodrich Company, Specialty Polymers & Chemicals Division, Cleveland, Ohio. Pemulen® materials include acrylate/C10-30 alkyl acrylate cross-polymers, or high molecular weight co-polymers of acrylic acid and a long chain alkyl methacrylate cross-linked with allyl ethers of pentaerythritol.

The presently useful polyanionic components may also be used to provide a suitable viscosity to the presently useful compositions. Thus, the polyanionic components may be useful in stabilizing the presently useful emulsions and in providing a suitable degree of viscosity to the presently useful compositions.

The polyelectrolyte or emulsion stabilizing component advantageously is present in an amount effective to at least assist in stabilizing the cyclosporin component-containing emulsion. For example, the polyelectrolyte/emulsion stabilizing component may be present in an amount in a range of about 0.01% by weight or less to about 1% by weight or more, preferably about 0.02% by weight to about 0.5% by weight, of the composition.

Any suitable tonicity component may be employed in accordance with the present invention. Preferably, such tonicity component is non-ionic, for example, in order to avoid interfering with the other components in the presently useful emulsions and to facilitate maintaining the stability of the emulsion prior to use. Useful tonicity agents include, without limitation, glycerine, mannitol, sorbitol and the like and mixtures thereof. The presently useful emulsions are preferably within the range of plus or minus about 20% or about 10% from being isotonic.

Ophthalmic demulcent components may be included in effective amounts in the presently useful compositions. For example, ophthalmic demulcent components such as carboxymethylcellulose, other cellulose polymers, dextran 70, gelatin, glycerine, polyethylene glycols (e.g., PEG 300 and PEG 400), polysorbate 80, propylene glycol, polyvinyl alcohol, povidone and the like and mixtures thereof, may be used in the present ophthalmic compositions, for example, compositions useful for treating dry eye.

The demulcent components are preferably present in the compositions, for example, in the form of eye drops, in an amount effective in enhancing the lubricity of the presently useful compositions. The amount of demulcent component in the present compositions may be in a range of at least about 0.01% or about 0.02% to about 0.5% or about 1.0% by weight of the composition.

Many of the presently useful polyelectrolyte/emulsion stabilizing components may also be effective as demulcent components, and vice versa. The emulsifier/surfactant components may also be effective as demulcent components and vice versa.

The pH of the emulsions can be adjusted in a conventional manner using sodium hydroxide and/or hydrochloric acid to a physiological pH level. The pH of the presently useful emulsions preferably is in the range of about 6 to about 10, more preferably about 7.0 to about 8.0 and still more preferably about 7.2 to about 7.6.

Although buffer components are not required in the presently useful compositions, suitable buffer components, for example, and without limitation, phosphates, citrates, acetates, borates and the like and mixtures thereof, may be employed to maintain a suitable pH in the presently useful compositions.

The presently useful compositions may include an effective amount of a preservative component. Any suitable preservative or combination of preservatives may be employed. Examples of suitable preservatives include, without limitation, benzalkonium chloride, methyl and ethyl parabens, hexetidine, phenyl mercuric salts and the like and mixtures thereof. The amounts of preservative components included in the present compositions are such to be effective in preserving the compositions and can vary based on the specific preservative component employed, the specific composition involved, the specific application involved, and the like factors. Preservative concentrations often are in the range of about 0.00001% to about 0.05% or about 0.1% (w/v) of the composition, although other concentrations of certain preservatives may be employed.

Very useful examples of preservative components in the present invention include, but are not limited to, chlorite components. Specific examples of chlorite components useful as preservatives in accordance with the present invention include stabilized chlorine dioxide (SCD), metal chlorites such as alkali metal and alkaline earth metal chlorites, and the like and mixtures thereof. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety by reference herein. Specific examples of useful SCD products include that sold under the trademark Dura Klor by Rio Linda Chemical Company, Inc., and that sold under the trademark Anthium Dioxide® by International Dioxide, Inc. An especially useful SCD is a product sold under the trademark Bio-Cide® by Bio-Cide International, Inc., as well as a product identified by Allergan, Inc. by the trademark Purite.

Other useful preservatives include antimicrobial peptides. Among the antimicrobial peptides which may be employed include, without limitation, defensins, peptides related to defensins, cecropins, peptides related to cecropins, magainins and peptides related to magainins and other amino acid polymers with antibacterial, antifungal and/or antiviral activities. Mixtures of antimicrobial peptides or mixtures of antimicrobial peptides with other preservatives are also included within the scope of the present invention.

The compositions of the present invention may include viscosity modifying agents or components, such as cellulose polymers, including hydroxypropyl methyl cellulose (HPMC), hydroxyethyl cellulose (HEC), ethyl hydroxyethyl cellulose, hydroxypropyl cellulose, methyl cellulose and carboxymethyl cellulose; carbomers (e.g. carbopol, and the like); polyvinyl alcohol; polyvinyl pyrrolidone; alginates; carrageenans; and guar, karaya, agarose, locust bean, tragacanth and xanthan gums. Such viscosity modifying components are employed, if at all, in an amount effective to provide a desired viscosity to the present compositions. The concentration of such viscosity modifiers will typically vary between about 0.01 to about 5% w/v of the total composition, although other concentrations of certain viscosity modifying components may be employed.

The presently useful compositions may be produced using conventional and well known methods useful in producing ophthalmic products including oil-in-water emulsions.

In one example, the oily phase of the emulsion can be combined with the cyclosporin component to solubilize the cyclosporin component in the oily material phase. The oily phase and the water may be separately heated to an appropriate temperature. This temperature may be the same in both cases, generally a few degrees to about 10° C. above the melting temperature of the ingredient(s) having the highest melting point in the case of a solid or semi-solid oily phase for emulsifier components in the oily phase. Where the oily phase is a liquid at room temperature, a suitable temperature for preparation of a composition may be determined by routine experimentation in which the melting point of the ingredients aside from the oily phase is determined. In cases where all components of either the oily phase or the water phase are soluble at room temperature, no heating may be necessary. Non-emulsifying agents which are water soluble are dissolved in the water and oil soluble components including the surfactant components are dissolved in the oily phase.

To create an oil-in-water emulsion, the final oil phase is gently mixed into either an intermediate, preferably de-ionized water, phase or into the final water phase to create a suitable dispersion and the product is allowed to cool with or without stirring. In the case where the final oil phase is first gently mixed into an intermediate water phase, the resulting emulsion concentrate is thereafter mixed in the appropriate ratio with the final aqueous phase. In such cases, the emulsion concentrate and the final aqueous phase may not be at the same temperature or heated above room temperature, as the emulsion may be already formed at this point.

The oil-in-water emulsions of the present invention can be sterilized after preparation using heat, for example, autoclave steam sterilization or can be sterile filtered using, for example, a 0.22 micron sterile filter.

Sterilization employing a sterilization filter can be used when the emulsion droplet (or globule or particle) size and characteristics allows this. The droplet size distribution of the emulsion need not be entirely below the particle size cutoff of the 0.22 micron sterile filtration membrane to be sterile-filtratable. In cases wherein the droplet size distribution of the emulsion is above the particle size cutoff of the 0.22 micron sterile filtration membrane, the emulsion needs to be able to deform or change while passing through the filtration membrane and then reform after passing through. This property is easily determined by routine testing of emulsion droplet size distributions and percent of total oil in the compositions before and after filtration. Alternatively, a loss of a small amount of larger droplet sized material may be acceptable.

The present oil-in-water emulsions preferably are thermodynamicaly stable, much like microemulsions, and yet may not be isotropic transparent compositions as are microemulsions. The emulsions of the present invention advantageously have a shelf life exceeding one year at room temperature.

The following non-limiting examples illustrate certain aspects of the present invention.

EXAMPLE 1

Two compositions are selected for testing. These compositions are produced in accordance with well known techniques and have the following make-ups:

| | Composition I wt % | Composition II wt % |
|---|---|---|
| Cyclosporin A | 0.1 | 0.05 |
| Castor Oil | 1.25 | 1.25 |
| Polysorbate 80 | 1.00 | 1.00 |
| Premulen ® | 0.05 | 0.05 |
| Glycerine | 2.20 | 2.20 |
| Sodium hydroxide | qs | qs |
| Purified Water | qs | qs |
| pH | 7.2-7.6 | 7.2-7.6 |
| Weight Ratio of Cyclosporin A to Castor Oil | 0.08 | 0.04 |

These compositions are employed in a Phase 3, double-masked, randomized, parallel group study for the treatment of dry eye disease.

The results of this study indicate that Composition II, in accordance with the present invention, which has a reduced concentration of cyclosporin A and a cyclosporin A to castor oil ratio of less than 0.08, provides overall efficacy in treating dry eye disease substantially equal to that of Composition I. This is surprising for a number of reasons. For example, the reduced concentration of cyclosporin A in Composition II would have been expected to result in reduced overall efficacy in treating dry eye disease. Also, the large amount of castor oil relative to the amount of cyclosporin A in Composition II might have been expected to cause increased eye irritation relative to Composition I. However, both Composition I and Composition II are found to be substantially non-irritating in use.

Using relatively increased amounts of castor oil, with reduced amounts of cyclosporin component, as in Composition II, is believed to take advantage of the benefits, for example the ocular lubrication benefits, of castor oil, as well as the presence of ricinoleic acid in the castor oil, to at least assist in treating dry eye syndrome in combination with cyclosporin A.

In addition, it is found that the high concentration of castor oil relative to cyclosporin component, as in Composition II, provides the advantage of more quickly or rapidly (for example, relative to a composition which includes only 50% as much castor oil) breaking down or resolving the emulsion in the eye, for example, as measured by split-lamp techniques to monitor the composition in the eye for phase separation. Such rapid break down of the emulsion in the eye reduces vision distortion as the result of the presence of the emulsion in the eye, as well as facilitating the therapeutic effectiveness of the composition in treating dry eye disease.

Using reduced amounts of cyclosporin A, as in Composition II, to achieve therapeutic effectiveness mitigates even further against undesirable side effects and potential drug interactions. Prescribing physicians can provide (prescribe) Composition II to more patients and/or with fewer restrictions and/or with reduced risk of the occurrence of adverse events, e.g., side effects, drug interactions and the like, relative to providing Composition I.

While this invention has been described with respect to various specific examples and embodiments, it is to be understood that the invention is not limited thereto and that it can be variously practiced within the scope of the following claims.

What is claimed is:

1. A method of treating dry eye disease, the method comprising topically administering to the eye of a human in need thereof an emulsion at a frequency of twice a day, wherein the emulsion comprises cyclosporin A in an amount of about 0.05% by weight, polysorbate 80, acrylate/C10-30 alkyl acrylate cross-polymer, water, and castor oil in an amount of about 1.25% by weight; and
   wherein the topical ophthalmic emulsion is effective in treating dry eye disease.

2. The method of claim 1, wherein the emulsion further comprises a tonicity agent or a demulcent component.

3. The method of claim 2, wherein the tonicity agent or the demulcent component is glycerine.

4. The method of claim 1, wherein the emulsion further comprises a buffer.

5. The method of claim 4, wherein the buffer is sodium hydroxide.

6. The method of claim 1, wherein the topical ophthalmic emulsion further comprises glycerine and a buffer.

7. The method of claim 1, wherein the emulsion comprises polysorbate 80 in an amount of about 1.0% by weight.

8. The method of claim 1, wherein the emulsion comprises acrylate/C10-30 alkyl acrylate cross-polymer in an amount of about 0.05% by weight.

9. The method of claim 1, wherein the emulsion further comprises glycerine in an amount of about 2.2% by weight and a buffer.

10. The method of claim 9, wherein the buffer is sodium hydroxide.

11. The method of claim 1, wherein, when the emulsion is administered to an eye of a human, the blood of the human has substantially no detectable concentration of cyclosporin A.

12. The method of claim 6, wherein the emulsion has a pH in the range of about 7.2 to about 7.6.

13. The method of claim 1, wherein the emulsion is as substantially therapeutically effective as a second emulsion administered to a human in need thereof at a frequency of twice a day, the second emulsion comprising cyclosporin A in an amount of 0.1% by weight and castor oil in an amount of 1.25% by weight.

14. The method of claim 1, wherein the emulsion achieves at least as much therapeutic effectiveness as a second emulsion administered to a human in need thereof a frequency of twice a day, the second emulsion comprising cyclosporin A in an amount of 0.1% by weight and castor oil in an amount of 1.25% by weight.

15. The method of claim 1, wherein the emulsion breaks down more quickly in the eye of a human, once administered to the eye of the human, thereby reducing vision distortion in the eye of the human as compared to a second emulsion that contains only 50% as much castor oil.

16. The method of claim 1, wherein the emulsion, when administered to the eye of a human, demonstrates a reduction in adverse events in the human, relative to a second emulsion administered to a human in need thereof a frequency of twice a day, the second emulsion comprising cyclosporin A in an amount of 0.1% by weight and castor oil in an amount of 1.25% by weight.

17. The method of claim 16, wherein the adverse events are side effects.

18. A method of reducing side effects in a human being treated for dry eye syndrome, the method comprising the step of topically administering to the eye of the human in need thereof an emulsion at a frequency of twice a day, wherein the emulsion comprises:
   cyclosporin A in an amount of about 0.05% by weight;
   castor oil in an amount of about 1.25% by weight;
   polysorbate 80 in an amount of about 1.0% by weight;
   acrylate/C10-30 alkyl acrylate cross-polymer in an amount of about 0.05% by weight;
   a tonicity component or a demulcent component in an amount of about 2.2% by weight;
   a buffer; and
   water;
   wherein the topical ophthalmic emulsion has a pH in the range of about 7.2 to about 7.6.

19. The method of claim 18, wherein the buffer is sodium hydroxide.

20. The method of claim 18, wherein the tonicity component or the demulcent component is glycerine.

21. The method of claim 18, wherein, when the emulsion is administered to the eye of a human for treating dry eye syndrome, the blood of the human has substantially no detectable concentration of the cyclosporin A.

22. The method of claim 18, wherein the emulsion is effective in treating dry eye disease.

23. A method of treating dry eye disease, the method comprising the step of topically administering to an eye of a human in need thereof an emulsion at a frequency of twice a day, the emulsion comprising:
   cyclosporin A in an amount of about 0.05% by weight;
   castor oil in an amount of about 1.25% by weight;
   polysorbate 80 in an amount of about 1.0% by weight;
   acrylate/C10-30 alkyl acrylate cross-polymer in an amount of about 0.05% by weight;
   glycerine in an amount of about 2.2% by weight;
   sodium hydroxide; and
   water;
   wherein the emulsion is effective in treating dry eye disease.

24. The method of claim 23, wherein the emulsion has a pH in the range of about 7.2 to about 7.6.

* * * * *

(12) INTER PARTES REVIEW CERTIFICATE (2104th)
United States Patent
Acheampong et al.

(10) Number: US 8,633,162 K1
(45) Certificate Issued: Jun. 11, 2021

(54) METHODS OF PROVIDING THERAPEUTIC EFFECTS USING CYCLOSPORIN COMPONENTS

(71) Applicants: Andrew Acheampong; Diane D. Tang-Liu; James N. Chang; David F. Power

(72) Inventors: Andrew Acheampong; Diane D. Tang-Liu; James N. Chang; David F. Power

(73) Assignee: SAINT REGIS MOHAWK TRIBE

Trial Numbers:

IPR2016-01130 filed Jun. 3, 2016
IPR2017-00583 filed Jan. 6, 2017
IPR2017-00599 filed Jan. 6, 2017

Inter Partes Review Certificate for:

Patent No.: 8,633,162
Issued: Jan. 21, 2014
Appl. No.: 13/967,179
Filed: Aug. 14, 2013

The results of IPR2016-01130 joined with IPR2017-00583 and IPR2017-00599 are reflected in this inter partes review certificate under 35 U.S.C. 318(b).

INTER PARTES REVIEW CERTIFICATE
U.S. Patent 8,633,162 K1
Trial No. IPR2016-01130
Certificate Issued Jun. 11, 2021

AS A RESULT OF THE INTER PARTES REVIEW PROCEEDING, IT HAS BEEN DETERMINED THAT:

Claims 1-24 are cancelled.

* * * * *